(12) United States Patent
Groves et al.

(10) Patent No.: US 10,595,976 B2
(45) Date of Patent: Mar. 24, 2020

(54) ORAL CARE DEVICE

(71) Applicant: Conopco, Inc., Englewood Cliffs, NJ (US)

(72) Inventors: Brian Joseph Groves, Wirral (GB); Adam John Limer, Northwich (GB); William John Wilson, Wirral (GB)

(73) Assignee: CONOPCO INC., Englewood Cliffs, NJ (US)

( * ) Notice: Subject to any disclaimer, the term of this patent is extended or adjusted under 35 U.S.C. 154(b) by 0 days.

(21) Appl. No.: 15/572,942

(22) PCT Filed: May 5, 2016

(86) PCT No.: PCT/EP2016/060125
§ 371 (c)(1),
(2) Date: Nov. 9, 2017

(87) PCT Pub. No.: WO2016/192924
PCT Pub. Date: Dec. 8, 2016

(65) Prior Publication Data
US 2018/0125626 A1 May 10, 2018

(30) Foreign Application Priority Data
Jun. 5, 2015 (EP) .................................. 15170828

(51) Int. Cl.
*A61K 8/24* (2006.01)
*A61C 19/06* (2006.01)
(Continued)

(52) U.S. Cl.
CPC .......... *A61C 19/063* (2013.01); *A61C 19/066* (2013.01); *A61K 8/0208* (2013.01);
(Continued)

(58) Field of Classification Search
CPC ....................................................... A61K 8/24
See application file for complete search history.

(56) References Cited

U.S. PATENT DOCUMENTS

| | | | |
|---|---|---|---|
| 4,083,955 A | 4/1978 | Grabenstetter et al. | |
| 4,713,243 A | 12/1987 | Schiraldi et al. | |

(Continued)

FOREIGN PATENT DOCUMENTS

| | | |
|---|---|---|
| CN | 1150881 | 5/1997 |
| CN | 1893915 | 1/2007 |

(Continued)

OTHER PUBLICATIONS

Co-pending Application, Groves et al., U.S. Appl. No. 15/572,930, dated Nov. 9, 2017, Oral Care Device.

(Continued)

*Primary Examiner* — Benjamin J Packard
(74) *Attorney, Agent, or Firm* — Foley & Lardner LLP

(57) ABSTRACT

A delivery system for delivering a enamel regeneration system to the surfaces of teeth the delivery system comprising a delivery device and a separate activator composition, the delivery device comprising; a strip of an orally acceptable flexible material, having a strip surface capable of being applied to a tooth surface, the strip having components of an enamel regeneration system deposited upon the strip surface thereof, and/or impregnated into its structure and the activator system comprising water.

20 Claims, 1 Drawing Sheet

(51) Int. Cl.
*A61K 8/25* (2006.01)
*A61K 8/02* (2006.01)
*A61K 8/73* (2006.01)
*A61Q 11/00* (2006.01)

(52) U.S. Cl.
CPC .............. *A61K 8/0233* (2013.01); *A61K 8/24* (2013.01); *A61K 8/25* (2013.01); *A61K 8/731* (2013.01); *A61Q 11/00* (2013.01)

(56) References Cited

U.S. PATENT DOCUMENTS

| | | | |
|---|---|---|---|
| 5,030,444 | A | 7/1991 | Hoyles et al. |
| 5,135,738 | A | 8/1992 | Gaffar |
| 5,605,675 | A | 2/1997 | Usen et al. |
| 5,853,704 | A | 12/1998 | Zhang et al. |
| 5,879,691 | A | 3/1999 | Sagel et al. |
| 6,159,448 | A | 12/2000 | Winston |
| 6,375,963 | B1 | 4/2002 | Repka et al. |
| 6,869,595 | B2 | 3/2005 | Kostinko et al. |
| 6,893,629 | B2 | 5/2005 | Prosise et al. |
| 7,662,363 | B2 | 2/2010 | Stanier |
| 8,257,721 | B2 | 9/2012 | Butler |
| 2002/0028251 | A1 | 3/2002 | Okay |
| 2003/0082114 | A1 | 5/2003 | Deng |
| 2004/0120903 | A1 | 6/2004 | Sagel et al. |
| 2004/0219190 | A1 | 11/2004 | Kosti |
| 2005/0137110 | A1 | 6/2005 | Scott |
| 2005/0186150 | A1 | 8/2005 | Allred |
| 2005/0249678 | A1 | 11/2005 | Hassan et al. |
| 2006/0099550 | A1 | 5/2006 | Faasse et al. |
| 2006/0292092 | A1 | 12/2006 | Sharma et al. |
| 2009/0271936 | A1 | 11/2009 | Walanski |
| 2010/0136067 | A1 | 6/2010 | Butler et al. |
| 2012/0259011 | A1 | 10/2012 | Misso |
| 2013/0171221 | A1 | 7/2013 | Deng |

FOREIGN PATENT DOCUMENTS

| | | |
|---|---|---|
| CN | 1913867 | 2/2007 |
| CN | 101600444 | 9/2009 |
| CN | 101600442 | 12/2009 |
| CN | 101600443 | 12/2009 |
| CN | 101663017 | 3/2010 |
| CN | 103079526 | 5/2013 |
| CN | 103079645 | 5/2013 |
| CN | 103476385 | 12/2013 |
| CN | 104244918 | 12/2014 |
| DE | 3942643 | 3/2008 |
| EP | 1736135 | 12/2006 |
| EP | 2089040 | 8/2009 |
| EP | 3021817 | 5/2016 |
| GB | 1408922 | 10/1975 |
| GB | 1516525 | 7/1978 |
| JP | 2011183043 | 9/2011 |
| WO | WO9807448 | 2/1998 |
| WO | WO2004045446 | 6/2004 |
| WO | WO2006004991 | 1/2006 |
| WO | WO2008015117 | 2/2008 |
| WO | WO2008068149 | 6/2008 |
| WO | WO2008068247 | 6/2008 |
| WO | WO2008068248 | 6/2008 |
| WO | WO2011109919 | 9/2011 |
| WO | WO2011160996 | 12/2011 |
| WO | WO2012003178 | 1/2012 |
| WO | WO2012031785 | 3/2012 |
| WO | WO2012031786 | 3/2012 |
| WO | WO2012143220 | 10/2012 |
| WO | WO2013034421 | 3/2013 |
| WO | WO2013096321 | 6/2013 |
| WO | WO2014170065 | 10/2014 |
| WO | WO2015007503 | 1/2015 |

OTHER PUBLICATIONS

Co-pending Application, Groves et al., U.S. Appl. No. 15/572,949, dated Nov. 9, 2017, Oral Care Device.
IPRP2 in PCTEP2016060124, Oct. 9, 2017 (NPL 1, pp. 1-11).
IPRP2 in PCTEP2016060125, Sep. 7, 2017 (NPL 1, pp. 12-36).
IPRP2 in PCTEP2016060126, Oct. 9, 2017 (NPL 1, pp. 37-55).
Search Report & Written Opinion in EP15170823, dated Mar. 11, 2016 (NPL 1, pp. 56-65).
Search Report & Written Opinion in PCTEP2016060125, dated Jul. 26, 2016 (NPL 4).
Search Report & Written Opinion in PCTEP2016060126, dated Jun. 8, 2016 (NPL 2, pp. 1-14).
Search Report (Partial) in EP15170828, dated Nov. 23, 2015 (NPL 2, pp. 15-21).
Search Report and Written Opinion in PCTEP2016060124, dated Jun. 24, 2016 NPL 2, p. 22-26).
Search Report in EP15170826, dated Nov. 19, 2015 (NPL 2, pp. 27-35).
Search Report in EP15170829, dated Nov. 23, 2015 (NPL 2, pp. 36-39).
Written Opinion 2 in PCTEP2016060124, dated May 19, 2017 (NPL 2, pp. 40-84).
Written Opinion2 in PCTEP2016060126, dated May 24, 2017 (NPL 3, pp. 1-14).
Written Opinion2 in PCTEP2016060125, dated May 19, 2017 (NPL 3, pp. 15-23).
Qiu Bingyi; Encyclopedia of Cosmetic Chemistry and Technology; Jun. 30, 1997; pp. 1374 No translation available; China Light Industry Press.
Search Report & Written Opinion in EP13177296; dated Dec. 18, 2013; European Patent Office (EPO).
Written Opinion in PCTEP201406376; dated Sep. 11, 2014.
Search Report in PCTEP201406376; dated Sep. 11, 2014.
IPRP2 in PCTEP2014063706; Jun. 19, 2015.

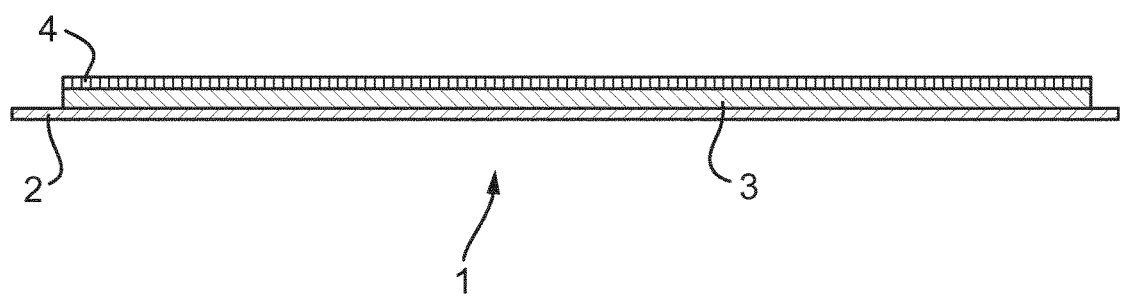

ORAL CARE DEVICE

FIELD OF THE INVENTION

The invention relates to an oral care products for the remineralisation and whitening of teeth.

BACKGROUND OF THE INVENTION

Teeth are important both functionally and aesthetically. There is a need for strong healthy teeth that appear white and glossy.

Calcium phosphate is the primary component of the enamel and dentin in the form of hydroxyapatite. In the mouth, there is a natural equilibrium between hydroxyapatite being dissolved from the enamel of teeth and hydroxyapatite being formed on or in the teeth from substances occurring naturally in the saliva. This equilibrium is shifting continuously, but diet and physical conditions can result in hydroxyapatite being dissolved arising in demineralisation.

If the equilibrium is such that hydroxyapatite is being formed, this is referred to as remineralisation. Remineralisation hardens and strengthens the teeth, thereby providing protection from and treatment for dental erosion and/or tooth wear. It also reduces the likelihood of tooth decay and improves the appearance of the teeth, in particular their whiteness. The teeth may also appear smoother and shinier as a result.

U.S. Pat. No. 5,605,675 discloses a process for remineralisation of dental enamel by application of a two-phase composition; one phase containing a water-soluble calcium compound and one phase containing a water soluble inorganic phosphate and a water-soluble fluorine compound.

U.S. Pat. No. 4,083,955 discloses a process for remineralisation of dental enamel by sequential application of two compositions, the first comprising calcium ions and second comprising phosphate ions, or vice versa.

However there remains the need for a simple and effective way to enable enamel regeneration of the teeth and to whiten the teeth.

SUMMARY OF THE INVENTION

Accordingly the present invention relates to a delivery system for delivering a enamel regeneration system to the surfaces of teeth the delivery system comprising a delivery device and a separate activator composition, the delivery device comprising; a strip of an orally acceptable flexible material, having a strip surface capable of being applied to a tooth surface, the strip having components of an enamel regeneration system deposited upon the strip surface thereof, and/or impregnated into its structure and the activator system comprising water.

DETAILED DESCRIPTION OF THE INVENTION

The delivery device of the invention comprises a strip of an orally acceptable flexible material. The surface of the strip is capable of being applied to a tooth surface.

Preferably the device has an elongate shape of a length sufficient that when placed against the front surface of a user's teeth it extends across a plurality of teeth, and of sufficient width that it extends at least from the gumline of the teeth to the crowns of the teeth. The elongate shape is such that it minimises the need for subsequent applications and time to cover all the user's teeth.

In a further embodiment the strip is such that it can be sufficient that when placed against the front surface of a user's teeth it extends across a plurality of teeth, and of sufficient width that it extends at least from the front gumline of the teeth to the crowns of the teeth and to the gumline behind the user's teeth leading to total coverage of the teeth above the gumline.

Preferably the application device is rectangular in shape.

Preferably the strip/device has the enamel regeneration system deposited upon the strip surface thereof as a layer or more preferably multiple layers.

In a preferred embodiment the device is a strip comprising a plurality of layers.

Preferably the device comprises at least two layers; one layer comprises a non-dissolving backing film, a second layer comprises a component of the enamel regeneration system. More preferably the strip comprises third protective layer it is particularly preferred if the third protective layer comprises a water soluble polymer.

It is preferable if the non-dissolving backing layer comprises materials such as polymers, natural and synthetic wovens, non-wovens, foil, paper, rubber, and combinations thereof. The strip of material may be a single layer of material or a laminate of more than one layer. Generally, the strip of material is substantially water impermeable. The material may be any type of polymer that is compatible with tooth whitening actives and is sufficiently flexible to be shaped and applied to the tooth surface. The material may comprise a single polymer or a mixtures of polymers. Suitable polymers include, but are not limited to, polyethylene, polypropylene, ethylvinylacetate, ethylvinyl alcohol, polyesters, polyamides, fluoroplastics and combinations thereof. Preferably, the material is polyethylene. The strip of material is generally less than about 1 mm thick, preferably less than about 0.05 mm thick, and more preferably from about 0.001 to about 0.03 mm thick.

It is preferable the strip has a second layer comprising components of the enamel regeneration system. It is advantageous if the component of the enamel regeneration system is a water insoluble and/or slightly soluble calcium source.

Soluble and insoluble calcium source, as used herein, refers to the solubility of the calcium source in water. Soluble means a source that dissolves in water to give a solution with a concentration of at least 0.1 moles per liter at room temperature. Insoluble means a source that dissolves in water to give a solution with a concentration of less than 0.001 moles per liter at room temperature. Slightly soluble, therefore, is defined to mean a source that dissolves in water to give a solution with a concentration of greater than 0.001 moles per liter at room temperature and less than 0.1 moles per liter at room temperature. Substantially free of, as used herein, means less than 1.5%, and preferably, less than 1.0%, and most preferably, from 0.0 to 0.75% by weight, based on total weight of the oral care composition, including all ranges subsumed therein. The calcium source suitable for use in this invention is limited only to the extent that the same may be used in an oral cavity. In a preferred embodiment, the calcium source employed is insoluble or slightly soluble in water, but most preferably, insoluble in water.

Illustrative examples of the types of calcium source that may be used in this invention include, for example, calcium phosphate (i.e., added), calcium gluconate, calcium oxide, calcium lactate, calcium carbonate, calcium hydroxide, calcium sulfate, calcium carboxymethyl cellulose, calcium alginate, calcium salts of citric acid, calcium silicate, mixtures thereof or the like. In a preferred embodiment the calcium source is calcium silicate. In a more preferred embodiment, the calcium silicate used is ($CaS_iO_3$) whereby the same is made commercially available under the name Microcal ET by Ineos Silicas, Ltd.

In yet another preferred embodiment, the calcium source is insoluble calcium silicate, present as the composite material calcium oxide-silica ($CaO$—$SiO_2$) as described in commonly-owned application Publication No. 2008/015117.

When a calcium silicate composite material is employed, the ratio of calcium to silicon (Ca:Si) may be from 1:10 to 3:1. The Ca:Si ratio is preferably from 1:5 to 2:1, and more preferably, from 1:3 to 2:1, and most preferably, from about 1:2 to 2:1. The calcium silicate may comprise mono-calcium silicate, bi-calcium silicate, or tri-calcium silicate whereby ratios of calcium to silicon (Ca:Si) should be understood to be atom ratios.

The calcium source employed in this invention may be in a crystalline or amorphous state, and preferably, the same is in an amorphous state. In an often preferred embodiment, the calcium source is in a mesoporous state, i.e. the source is a material having pores with diameters from 1 nm to 50 microns. Mesoporous calcium silicate (MCS) is often preferred.

The MCS which may be used in this invention can be made by combining a calcium salt, a silica precursor like silicate and a structure-directing agent to yield a solid suitable for calcinating. A more detailed description of the process that may be conducted to make the MCS suitable for use in this invention is described in the aforementioned commonly-owned application, Publication No. WO 2008/015117.

The amount of calcium source in the composition present as the second layer of this invention is typically from 0.1 to 50%, and preferably, from 1 to 30%, and most preferably, from 5 to 20% by weight of the oral care composition based on total weight of the oral care composition and including all ranges subsumed therein.

It is highly preferable if the second layer is non-aqueous, that is that the composition comprises less than 1 wt % of the total composition of the second layer of water, preferably less than 0.5 wt % of water.

It is highly preferable if the second layer is sandwiched between the first backing layer and a third layer.

It is preferable if the device comprises a third layer. The third layer preferably comprises a water soluble polymer or polymers. Suitable water soluble polymers may be natural or synthetic. Suitable natural hydrocolloids and water soluble polymers include cellulosic material, a polysaccharide, a gum, a protein, a starch or a glucan. Examples include but are not limited to carboxymethyl cellulose, hydroxyl methyl cellulose, hydroxyethyl cellulose, hydroxypropyl cellulose, hydroxypropylmethyl cellulose, gum Arabic, xanthan gum, karaya gum, tragacanth, acacia, carrageenan, guar gum, locust bean gum, pectin, alginates, polydextrose, dextrin, dextran, amylose, chitin, chitosan, levan, elsinan, collagen, gelatin, zein, gluten, soy protein isolate, whey protein isolate, casein and pullan. Suitable water soluble synthetic polymers include but are not limited to poly(vinyl pyrrolidone), poly(vinyl alcohol), poly(acrylic acid), polyacrylates, Methylmethacrylate copolymer, carboxyvinyl polymer, polyethylene oxide and polyethylene glycol. The water soluble polymer layer is preferably a mixture of methylcellulose and hydroxypropyl methylcellulose.

The advantage of having a water soluble layer and a non-water soluble layer is that in the mouth the water soluble layer dissolves in the saliva and the ingredients enclosed therein (the phosphate) can react with the ingredients in the second layer (silicate) to aid the in-situ regeneration of enamel on the teeth. Thus the system provides an enamel regeneration system that can be used with the minimum of water, can be easily stored and is stable on storage.

Preferably the composition of the invention comprises titanium dioxide. Preferably the titanium dioxide is present in the second layer of the device. A preferred form of titanium dioxide is calcium silicate coated $TiO_2$. Examples of preferred forms of calcium silicate coated TO02 are disclosed in WO2012/031786 and WO2012/031785.

It is preferable if the thickness of the first layer is less than about 1 mm thick, preferably less than about 0.05 mm thick, and more preferably from about 0.001 to about 0.03 mm thick, second layer is less than about 1 mm thick, preferably less than about 0.5 mm thick, and more preferably from about 0.001 to about 0.3 mm thick and third layer (if present) is less than about 1 mm thick, preferably less than about 0.5 mm thick, and more preferably from about 0.001 to about 0.3 mm thick.

The activator serum comprises an aqueous base formulation. The activator serum preferably comprises a phosphate source. The phosphate source that may be used in this invention is limited only to the extent that the same may be used in a composition suitable for use in an oral cavity. Illustrative examples of the types of phosphate source suitable for use in this invention include monosodium phosphate, sodium dihydrogen phosphate, disodium hydrogen phosphate, sodium pyrophosphate, tetrasodium pyrophosphate, sodium tripolyphosphate, sodium hexametaphosphate, potassium dihydrogenphosphate, trisodium phosphate, tripotassium phosphate, mixtures thereof or the like. The phosphate source is preferably one which is water soluble.

Typically, the phosphate source makes up from 0.5 to 15%, and preferably, from 2 to 12%, and most preferably, from 4 to 9% by weight of the composition used in the third layer, based on total weight of the composition of the third layer and including all ranges subsumed therein. In a preferred embodiment, the phosphate source used is one which results in an oral care composition having a pH from 5.5 to 8, preferably from 6 to 7.5, and most preferably, about neutral. In a most preferred embodiment, the phosphate source used is trisodium phosphate and monosodium dihydrogen phosphate at a trisodium phosphate to monosodium dihydrogen phosphate weight ratio of 1:4 to 4:1, preferably 1:3 to 3:1, and most preferably, from 1:2 to 2:1, including all ratios subsumed therein.

It is preferable if the composition of the activator comprises an aqueous base, that is that the composition comprises greater than 50 wt % of the serum composition of water, more preferably greater than 70 wt %.

The oral care composition described herein may comprise ingredients which are common in the art, such as:
  antimicrobial agents, e.g. Triclosan, chlorhexidine, copper-, zinc- and stannous salts such as zinc citrate, zinc sulphate, zinc glycinate, sodium zinc citrate and stannous pyrophosphate, sanguinarine extract, metronidazole, quaternary ammonium compounds, such as cetylpyridinium chloride; bis-guanides, such as chlorhexidine digluconate, hexetidine, octenidine, alexidine; and halogenated bisphenolic compounds such as 2,2' methylenebis-(4-chloro-6-bromophenol);
  anti-inflammatory agents such as ibuprofen, flurbiprofen, aspirin, indomethacin, etc.;
  anti-caries agents such as sodium trimetaphosphate and casein;
  plaque buffers such as urea, calcium lactate, calcium glycerophosphate and polyacrylates;

vitamins such as Vitamins A, C and E;
plant extracts;
desensitizing agents, e.g. potassium citrate, potassium chloride, potassium tartrate, potassium bicarbonate, potassium oxalate, and potassium nitrate;
anti-calculus agents, e.g. alkali-metal pyrophosphates, hypophosphite-containing polymers, organic phosphonates and phosphocitrates, etc;
biomolecules, e.g. bacteriocins, antibodies, enzymes, etc;
flavors, e.g., peppermint and spearmint oils;
proteinaceous materials such as collagen;
preservatives;
opacifying agents;
coloring agents like FD&C blue, yellow and/or red dyes/colorants;
pH-adjusting agents;
sweetening agents;
surfactants, such as anionic, cationic and zwitterionic or amphoteric surfactants (e.g., sodium lauryl sulfate, sodium dodecylbenzene sulfonate);
particulate abrasive materials such as abrasive silicas, aluminas, calcium carbonates, zirconium silicate, polymethylmethacrylate, dicalciumphosphates, calcium pyrophosphates, hydroxyapatites, trimetaphosphates, insoluble hexametaphosphates as well as agglomerated particulate abrasive materials;
fluoride sources like sodium fluoride, stannous fluoride, sodium monofluorophosphate, zinc ammonium fluoride, tin ammonium fluoride, calcium fluoride, cobalt ammonium fluoride or mixtures thereof;
polymeric compounds which can enhance the delivery of active ingredients such as antimicrobial agents can also be included. Examples of such polymers are copolymers of polyvinylmethylether with maleic anhydride and other similar delivery enhancing polymers, e.g., those described in DE-A03,942,643; buffers and salts to buffer the pH and ionic strength of the oral care compositions; and
other optional ingredients that may be included are, e.g., bleaching agents such as peroxy compound, e.g., potassium peroxydiphosphate, effervescing systems such as sodium bicarbonate/citric acid systems, color change systems, and the like.

Such ingredients common in the art typically and collectively make-up less than 20% by weight of the oral care composition, and preferably, from 0.0 to 15% by weight, and most preferably, from about 0.01 to about 12% by weight of the oral care composition, including all ranges subsumed therein.

Suitable carrier humectants are preferably used in the oral care composition of the present invention and they include, for example, glycerin, sorbitol, propylene glycol, dipropylene glycol, diglycerol, triacetin, mineral oil, polyethylene glycol (preferably, PEG-400), alkane diols like butane diol and hexanediol, ethanol, pentylene glycol, or a mixture thereof. The carrier humectants should, in any case, be substantially free of water, and preferably, anhydrous. The same, for example, can be used in solid form, whereby glycerin is the preferred carrier humectant. Such carriers are particularly suitable in compositions used in the second layer.

The carrier humectant is used to take the balance of the compositions up to 100%, and the same may be present in the range of from 10 to 90% by weight of the oral care composition. Preferably, the carrier humectant makes up from 25 to 80%, and most preferably, from 45 to 70% by weight of the oral care composition, based on total weight of the oral care composition and including all ranges subsumed therein.

The composition used in the layers of the invention are prepared by conventional methods of making oral care formulations. Such methods include mixing the ingredients under moderate shear and atmospheric pressure.

Mode of Use

The invention provides a method of whitening and remineralising teeth. The activator serum is applied to the strips of the invention. The activated strips as described above are applied to the surface of the teeth in sustained contact.

In the context of the present invention sustained contact means the product is left on the teeth for 1 to 60 minutes, preferably, about 5 to 45 minutes, more preferably 10 to 30 minutes before being removed.

Preferably the application of the oral care product of the invention is carried out once daily for a period of several consecutive days, in addition to a regular regime of tooth brushing (preferably at least twice daily).

Typically, use (for a period of about two weeks to one month) of the device with the oral care composition of the present invention will result in a new hydroxyapatite layer on teeth that is from 0.5 to 20 microns, and preferably, from 0.75 to 5 microns, including all ranges subsumed therein.

Detailed Description of Non-Limiting Embodiments

The invention, however, may be best understood by reference to the following description of some embodiments of the invention taken in conjunction with the accompanying drawing FIGURE in which FIG. 1 is a cross sectional view of the strip.

Referring to FIG. 1, a device (1) of the invention is shown in section. The device comprises a strip 2 of insoluble backing material, this can be considered the bottom layer Coated onto the insoluble backing material (2) is a second layer (3) comprising calcium silicate and titanium dioxide composite, a third protective layer (4) is present as the top layer in contact with the second layer.

The invention will now be illustrated by the following non-limiting Examples:

EXAMPLES

A simulated oral fluid was prepared by adding 1.9 L of water to a glass beaker. The following materials were added one by one with continuous stirring, allowing sufficient time for each chemical to fully dissolve before adding the next. Sodium chloride 16.07 g, sodium hydrogen carbonate 0.7 g, potassium chloride 0.448 g, potassium hydrogen phosphate 2.56 g, magnesium chloride hexahydrate 0.622 g, 1M hydrochloric acid 40 ml, calcium chloride 0.1998 g and sodium sulfate 0.1434 g. The pH was adjusted to 7.0 using saturated TRIS buffer and the total volume made up to 2 L using a volumetric flask.

Formulation and Processing: Polymer Film

| Ingredient | % w/w |
| --- | --- |
| Glycerol | 2.0 |
| Carboxy cellulose | 4.0 |
| Methyl cellulose | 4.0 |
| water | 90 |
| Total | 100 |

The water and glycerol was weighed into a beaker. The polymers added slowly while under shear using a Silverson LR4 bench top mixer and mixed until the polymer is fully dispersed (no lumps visible).

NB Air can become entrapped in the solution if required this can be removed using a desiccator.

To cast the film a quantity of the solution is poured on to a glass tile and using a pull down gauge the correct film height is achieved (micrometers on the gauge set at 15). The glass tiles are then placed in an oven at 50-60 Deg C. over night to remove the water.

The following day the film can be removed from the tile and cut to the appropriate size.

Formulation and Processing: Conc Tio2/Cs Slurry

| Ingredient | % w/w |
| --- | --- |
| Glycerol | 59.7 |
| Calcium Silicate | 15.0 |
| Calcium silicate coated TiO2 | 20.0 |
| Xanthan | 0.3 |
| Total | 100 |

The glycerol and Xanthan were added to the Esco-Labor 1 L mixing vessel and stirring at 65° C. for 30 minutes to disperse the xanthan gum. Once the Xanthan has been fully dispersed the remaining powders are added slowly and mixed to remove any lumps.

Formulation and Processing: Activator Solution for the Dropper

| Ingredient | % w/w |
| --- | --- |
| water | 95.1 |
| Trisodium phosphate | 1.63 |
| Monosodium phosphate | 1.37 |
| Cellulose Gum | 1.0 |
| Ethylhexyl glycerine | 0.3 |
| Benzyl Alcohol | 0.3 |
| Phenoxy Ethanol | 0.3 |
| Total | 100 |

Water was added to an Esco-Labor 1 L mixing vessel followed by the Sensiva SC50, Ethoxyethanol and Benzyl Alcohol and mixed to disperse. Subsequently SCMC was slowly added to the vessel through the port in the vessel lid and mixed to disperse.

The multilayer film was produced as follows.
Stage 1 a piece of plastic film (polyethylene) was cut to the appropriate size.
Stage 2 a piece of the polymer film was cut to size (wt=0.01 g).
Stage 3 using a small paint brush the conc slurry was painted on to one side of the film (wt of material 0.136 g) and then placed on top of the plastic film.

To a strip sample was added 0.5 ml activator solution via auto-pipette and immediately three 6×6 mm enamel block samples were placed on the surface. The samples were left in contact with the strip for 30 minutes with gentle agitation at 5 and 15 minutes. This procedure was completed twice, so n=6 enamel blocks were tested. After 30 minutes the bovine blocks were rinsed in 40 ml water and mixed gently for 1 minute. Samples were then incubated in simulated oral fluid for 5 hours. The application process was repeated 5 times in total. Colour was measured via chromameter at baseline and after strip application and incubation. L*a*b* colour parameters were converted to WIO whiteness indices to allow comparison between samples. Colour change is expressed as ΔWIO=WIO(slurry application)−WIO(baseline).

| | 1 Application | 3 Applications | 5 Applications |
| --- | --- | --- | --- |
| Whitening Change | 1.60 ± 0.65 | 4.05 ± 0.41 | 4.42 ± 1.28 |

The invention claimed is:

1. A delivery system for delivering an enamel regeneration system to the surfaces of teeth, the delivery system comprising:
   a delivery device comprising:
      a first layer comprising a strip of an orally acceptable non-dissolving, flexible, backing film, the strip comprising a strip surface capable of being applied to a tooth surface;
      a non-water soluble second layer comprising a component of an enamel regeneration system; and
      a water soluble third layer comprising a water soluble polymer; and
   a separate activator composition comprising water;
   wherein the component comprises a calcium source and the activator further comprises a phosphate source.

2. The delivery system of claim 1, wherein the calcium source is calcium silicate.

3. The delivery system of claim 1, wherein the water soluble polymer comprises a cellulosic material.

4. The delivery system of claim 1, wherein the device further comprises a tooth whitening substance.

5. The delivery system of claim 4, wherein the tooth whitening substance is titanium dioxide.

6. The delivery system of claim 4, wherein the tooth whitening substance is present in the non-water soluble second layer together with the component.

7. The delivery system of claim 1, wherein at least one of the first layer, the non-water soluble second layer, or the water soluble third layer has an elongate shape of a length sufficient to extend across a plurality of front surfaces of teeth and a width sufficient to extend from a gumline of a tooth to a crown of the tooth.

8. The delivery system of claim 1, wherein at least one of the first layer, the non-water soluble second layer, or the water soluble third layer is substantially rectangular.

9. The delivery system of claim 2, wherein the calcium source comprises pores with diameters that are between 1 nm and 50 μm, inclusive.

10. The delivery system of claim 1, wherein:
   the first layer is constructed from a polymer; and
   the strip has a thickness that is between 0.001 mm and 0.03 mm, inclusive.

11. The delivery system of claim 1, wherein the non-water soluble second layer is positioned between the first layer and the water soluble third layer such that the water soluble third layer covers the component.

12. The delivery system of claim 1, wherein the strip is water impermeable.

13. The delivery system of claim 1, wherein:
   the component further comprises an ingredient and a carrier humectant;
   the component has a first weight;
   the calcium source has a second weight; and
   the second weight is between 0.1% and 50%, inclusive, of the first weight.

14. The delivery system of claim 13, wherein the second weight is between 1% and 30%, inclusive, of the first weight.

15. The delivery system of claim 13, wherein the second weight is between 5% and 20%, inclusive, of the first weight.

16. The delivery system of claim 13, wherein the ingredient is at least one of an antimicrobial agent, an anti-inflammatory agent, an anti-caries agent, a plaque buffer, a vitamin, a plant extract, a desensitizing agent, an anti-calculus agent, a biomolecule, a flavor, a proteinaceous material, a preservative, an opacifying agent, a color agent, a pH-adjusting agent, a sweetening agent, a surfactant, a particulate abrasive material, a fluoride source, or a polymeric component.

17. The delivery system of claim 16, wherein:
the ingredient has a third weight; and
the third weight is between 0% and 20%, inclusive, of the first weight.

18. The delivery system of claim 17, wherein:
the carrier humectant has a fourth weight;
the second weight is between 5% and 20%, inclusive, of the first weight; and
the fourth weight is between 60% and 95%, inclusive, of the first weight.

19. The delivery system of claim 17, wherein the second weight is between 0.01% and 12%, inclusive, of the first weight.

20. The delivery system of claim 19, wherein:
the carrier humectant has a fourth weight;
the second weight is between 5% and 20%, inclusive, of the first weight; and
the fourth weight is between 68% and 94.99%, inclusive, of the first weight.

* * * * *